United States Patent
Smith et al.

(10) Patent No.: US 9,939,411 B2
(45) Date of Patent: Apr. 10, 2018

(54) EXTENDED REACH INSPECTION APPARATUS

(71) Applicant: The Boeing Company, Chicago, IL (US)

(72) Inventors: Nathan R. Smith, St. Charles, MO (US); Gary E. Georgeson, Tacoma, WA (US); Paul S. Rutherford, Maple Valley, WA (US); Jeffrey R. Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 218 days.

(21) Appl. No.: 14/803,758

(22) Filed: Jul. 20, 2015

(65) Prior Publication Data
US 2015/0323501 A1  Nov. 12, 2015

Related U.S. Application Data

(63) Continuation-in-part of application No. 13/547,190, filed on Jul. 12, 2012, now Pat. No. 9,086,386.

(51) Int. Cl.
*G01D 21/00* (2006.01)
*G01N 27/90* (2006.01)
(Continued)

(52) U.S. Cl.
CPC .......... *G01N 27/902* (2013.01); *B25J 9/0027* (2013.01); *B25J 9/1697* (2013.01);
(Continued)

(58) Field of Classification Search
CPC .. G01N 21/954; G01N 27/902; G01N 29/225; G01N 29/265; G01N 2291/2694;
(Continued)

(56) References Cited

U.S. PATENT DOCUMENTS

| | | | | |
|---|---|---|---|---|
| 2,053,837 A | * | 9/1936 | Langsner | G01O 5/00 33/284 |
| 3,534,591 A | | 10/1970 | Phelan | |
| 4,139,822 A | * | 2/1979 | Urich | G01N 27/9033 324/219 |
| 4,501,522 A | * | 2/1985 | Causer | B25J 3/04 414/4 |

(Continued)

FOREIGN PATENT DOCUMENTS

| | | |
|---|---|---|
| CH | 599533 A | 5/1978 |
| EP | 0487253 A1 | 5/1992 |

(Continued)

*Primary Examiner* — Benjamin Schmitt
(74) *Attorney, Agent, or Firm* — Charles L. Moore; Moore & Van Allen PLLC

(57) ABSTRACT

An extended reach inspection apparatus may include a scanner device and a robotic manipulator arm. The robotic manipulator arm may include a plurality of arm segments including a distal end arm segment and a proximal end arm segment. A movable joint may couple the distal end arm segment to the robotic manipulator arm. A telescoping extension mechanism may be coupled to the distal end arm segment. The scanner device is mounted to the telescoping extension mechanism for moving the scanner device between a retracted position proximate the robotic manipulator arm and an extended position at a distance from the robotic manipulator arm. A control handle may be coupled to the proximal end arm segment of the plurality of arm segments for manipulating the robotic manipulator arm.

20 Claims, 16 Drawing Sheets

(51) Int. Cl.
  *B25J 9/16* (2006.01)
  *B25J 18/02* (2006.01)
  *G01N 21/954* (2006.01)
  *G01N 29/22* (2006.01)
  *G01N 29/265* (2006.01)
  *B25J 9/00* (2006.01)
  *B25J 13/02* (2006.01)

(52) U.S. Cl.
  CPC .......... *B25J 18/025* (2013.01); *G01N 21/954* (2013.01); *G01N 29/225* (2013.01); *G01N 29/265* (2013.01); *B25J 9/0096* (2013.01); *B25J 13/02* (2013.01); *G01N 2291/0289* (2013.01); *G01N 2291/2694* (2013.01)

(58) Field of Classification Search
  CPC ....... G01D 11/30; B25J 9/0027; B25J 9/0096; B25J 9/02; B25J 9/1035; B25J 9/1697; B25J 13/02; B25J 18/025; B25J 19/02; B25J 19/023; B25J 19/04
  USPC ............ 73/865.8, 866.5; 901/15, 28, 44, 46
  See application file for complete search history.

(56) References Cited

U.S. PATENT DOCUMENTS

| | | | |
|---|---|---|---|
| 4,625,165 A | 11/1986 | Rothstein | |
| 4,643,029 A | 2/1987 | Klinvex | |
| 4,710,710 A | 12/1987 | Flora et al. | |
| 5,125,789 A * | 6/1992 | Farr | ......................... B25J 9/023 414/728 |
| 5,207,005 A | 5/1993 | Amos et al. | |
| 6,619,118 B1 | 9/2003 | Keck | |
| 7,340,971 B2 | 3/2008 | Carter et al. | |
| 7,659,715 B2 | 2/2010 | Briffa et al. | |
| 8,109,160 B2 | 2/2012 | Bossi et al. | |
| 8,176,808 B2 * | 5/2012 | Fisk | ......................... B25J 5/005 74/490.03 |
| 8,493,064 B2 | 7/2013 | Setbacken et al. | |
| 8,513,943 B2 | 8/2013 | Gehlen et al. | |
| 2009/0307918 A1 | 12/2009 | Rogers et al. | |

FOREIGN PATENT DOCUMENTS

| | | |
|---|---|---|
| JP | 57106476 A | 7/1982 |
| JP | 06268034 A | 9/1994 |
| JP | 0735808 A | 2/1995 |
| JP | 2010025801 A | 2/2010 |
| SU | 728115 A1 | 4/1980 |

* cited by examiner

EXTENDED REACH INSPECTION APPARATUS

CROSS REFERENCE TO RELATED APPLICATIONS

The present application is a continuation-in-part application of U.S. application Ser. No. 13/547,190, filed Jul. 12, 2012 (now U.S. Pat. No. 9,086,386), the contents of which are hereby incorporated by reference in their entirety.

FIELD

The present disclosure relates to nondestructive inspection/evaluation (NDI/NDE), and more particularly to an extended reach apparatus and sensors used in NDI/NDE that detect defects in structures and parts.

BACKGROUND

Increases in the complexity of aerospace structures have made NDI/NDE, which terms are used interchangeably herein, more and more difficult to apply successfully and cost-effectively. Often, a region of a particular structure requires inspection, but is inaccessible for the application of conventional NDE methods. In some cases, inspection requirements of regions with limited access have prompted part removal to improve access, or expensive redesigns altogether. Conventional tools include extenders and manipulation arms to reach into limited access areas and to aid probe placement on or near limited access areas of aircraft. Such areas may be cavities or obstructed areas, and include, for example, the interior of aircraft wings.

When in operation, certain sensors for detection of defects in a surface are preferably seated on the surface, or at least require maintaining no more than a maximum clearance from the surface. When a sensor, for example an eddy current sensor, is not completely seated on the surface, which may be referred to as "lift-off," the result may be a reduced sensitivity to small cracks.

A sensor may be applied to a surface that is not completely flat and require movement of the probe along the surface, or may be mounted to a rotating end of a probe for NDE in limited access areas. Either case may result in lift-off. For the rotating application, if the probe end is not exactly perpendicular to the surface to be inspected, the rotating path of the sensor will be eccentric; although the sensor may be flush with the surface at one point along the path, at an opposite point on the path (or some other location) there will be lift-off. Accordingly, an apparatus is needed that addresses lift-off to provide adequate sensitivity for detection of defects over the full range of motion of the sensor.

SUMMARY

In accordance with an embodiment, an extended reach inspection apparatus may include a scanner device and a robotic manipulator arm. The robotic manipulator arm may include a plurality of arm segments including a distal end arm segment and a proximal end arm segment. A movable joint may couple the distal end arm segment to the robotic manipulator arm. A telescoping extension mechanism may be coupled to the distal end arm segment. The scanner device is mounted to the telescoping extension mechanism for moving the scanner device between a retracted position proximate to the robotic manipulator arm and an extended position at a distance from the robotic manipulator arm. A control handle may be coupled to the proximal end arm segment of the plurality of arm segments for manipulating the robotic manipulator arm.

In accordance with another embodiment, an extended reach inspection apparatus may include a robotic manipulator arm and a scanner device. The scanner device is coupled to the robotic manipulator arm. The scanner device may include a probe having a longitudinal axis, a first end, and a second, free end defining an opening, wherein the opening is offset from the longitudinal axis. The scanner device may also include a sensor for inspecting a target and providing an electrical output. The sensor is received in the opening and when the probe is rotated about the longitudinal axis, the sensor moves in a substantially circular path. The scanner device may additionally include a bias means received in the opening in-between the first end of the probe and the sensor to urge the sensor away from the first end of the probe.

In accordance with another embodiment, a method may include inserting a robotic manipulator arm through at least one inspection port of an enclosed structure. The robotic manipulator arm may include a plurality of arm segments and a telescoping extension mechanism coupled to a distal end arm segment of the plurality of arm segments. A scanner device is mounted to the telescoping extension mechanism for moving the scanner device between a retracted position proximate to the robotic manipulator arm and an extended position at a distance from the robotic manipulator arm for performing an inspection. The method may also include operating a movable joint that couples the distal segment to the robotic manipulator arm to position the scanner relative to a component for performing the inspection. The method may additionally include moving the telescoping extension mechanism to position the scanner over the component for performing the inspection.

In accordance with an embodiment and any of the previous embodiments, the telescoping extension mechanism may include a base platform. The scanner device may be coupled to one side of the base platform and a track follower may be mounted to an opposite side of the base platform. The telescoping extension mechanism may also include a telescope extension track mounted to the distal end arm segment of the robotic manipulator arm. The track follower is configured to move along the telescope extension track between the retracted position and the extended position. The telescoping extension mechanism may also include a motor that moves the track follower along the telescope extension track. The controller controls the motor to move the scanner device between the retracted position and the extended position.

In accordance with an embodiment and any of the previous embodiments, the distal end arm segment may include a stationary portion coupled to the robotic manipulator arm by the movable joint and a rotatable portion rotationally coupled to the stationary portion. The distal end arm segment includes a longitudinal axis defined through the stationary portion and the rotatable portion. The rotatable portion is rotatable about the longitudinal axis relative to the stationary portion. The extended reach inspection apparatus may also include an indexing feature for determining an angle of rotation of the rotatable portion relative to the stationary portion.

In accordance with an embodiment and any of the previous embodiments, the extended reach apparatus may also include a midspar support apparatus configured to support the robotic manipulator arm between two spars of an enclosed structure. The midspar support apparatus may include a head fitting configured to releasably attach to an inspection port support member and the inspection port support member may be releasably attachable to a first inspection port in a first spar. The midspar support apparatus may also include a plurality of collapsible leg members extending from the head fitting. The plurality of collapsible leg members may be configured to contact a second spar opposite the first spar. The plurality of collapsible leg members are collapsible to fit through a second inspection port in the second spar.

Other aspects and features of the present disclosure, as defined solely by the claims, will become apparent to those ordinarily skilled in the art upon review of the following non-limited detailed description of the disclosure in conjunction with the accompanying figures.

BRIEF DESCRIPTION OF THE DRAWINGS

The following detailed description of embodiments refers to the accompanying drawings, which illustrate specific embodiments of the disclosure. Other embodiments having different structures and operations do not depart from the scope of the present disclosure.

DETAILED DESCRIPTION

Figure 1:
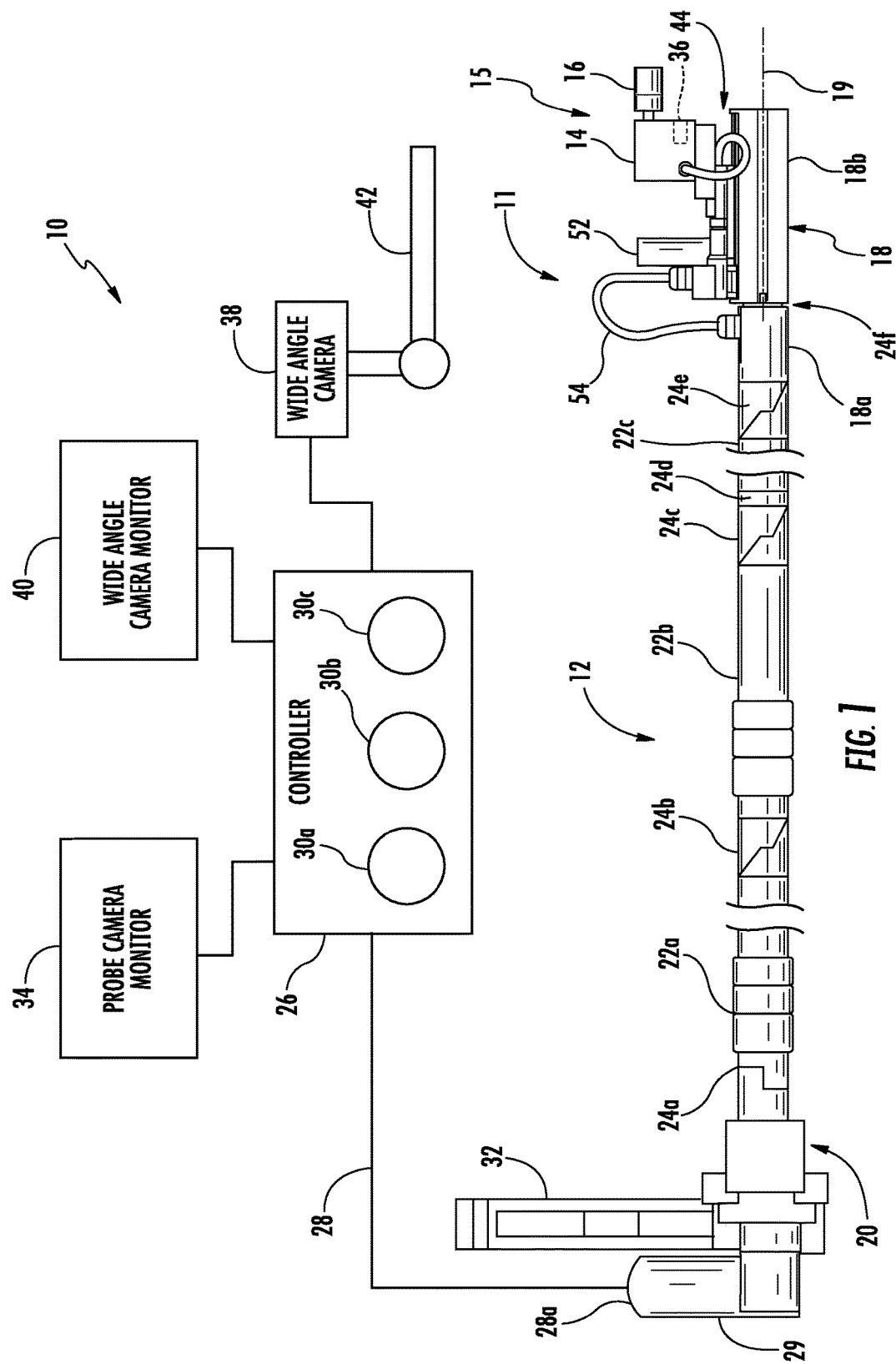
FIG. 1 is an example of an NDI/NDE system and side view of an example of a robotic manipulator arm of the NDI/NDE system including a scanner device with a probe in accordance with an embodiment of the present disclosure.

The following detailed description of embodiments refers to the accompanying drawings, which illustrate specific embodiments of the disclosure. Other embodiments having different structures and operations do not depart from the scope of the present disclosure. Like reference numerals may refer to the same element or component in the different drawings.

Certain terminology is used herein for convenience only and is not to be taken as a limitation on the embodiments described. For example, words such as "proximal", "distal", "top", "bottom", "upper," "lower," "left," "right," "horizontal," "front," "back," "vertical," "upward," and "downward" merely describe the configuration shown in the figures or relative positions. The referenced components may be oriented in any direction and the terminology, therefore, should be understood as encompassing such variations unless specified otherwise.

FIG. 1 is an example of an NDI/NDE system 10 including an example of an extended reach inspection apparatus 11 in accordance with an embodiment of the present disclosure. The extended reach inspection apparatus 11 may include a robotic manipulator arm 12 and an end effector 15. The end effector 15 may include a scanner device 14 with an inspection probe 16. The scanner device 14 may include any type of NDI/NDE inspection or scanning device, such as for example an eddy current inspection device, ultrasonic inspection device, x-ray inspection device or other NDI/

Figure 7A:
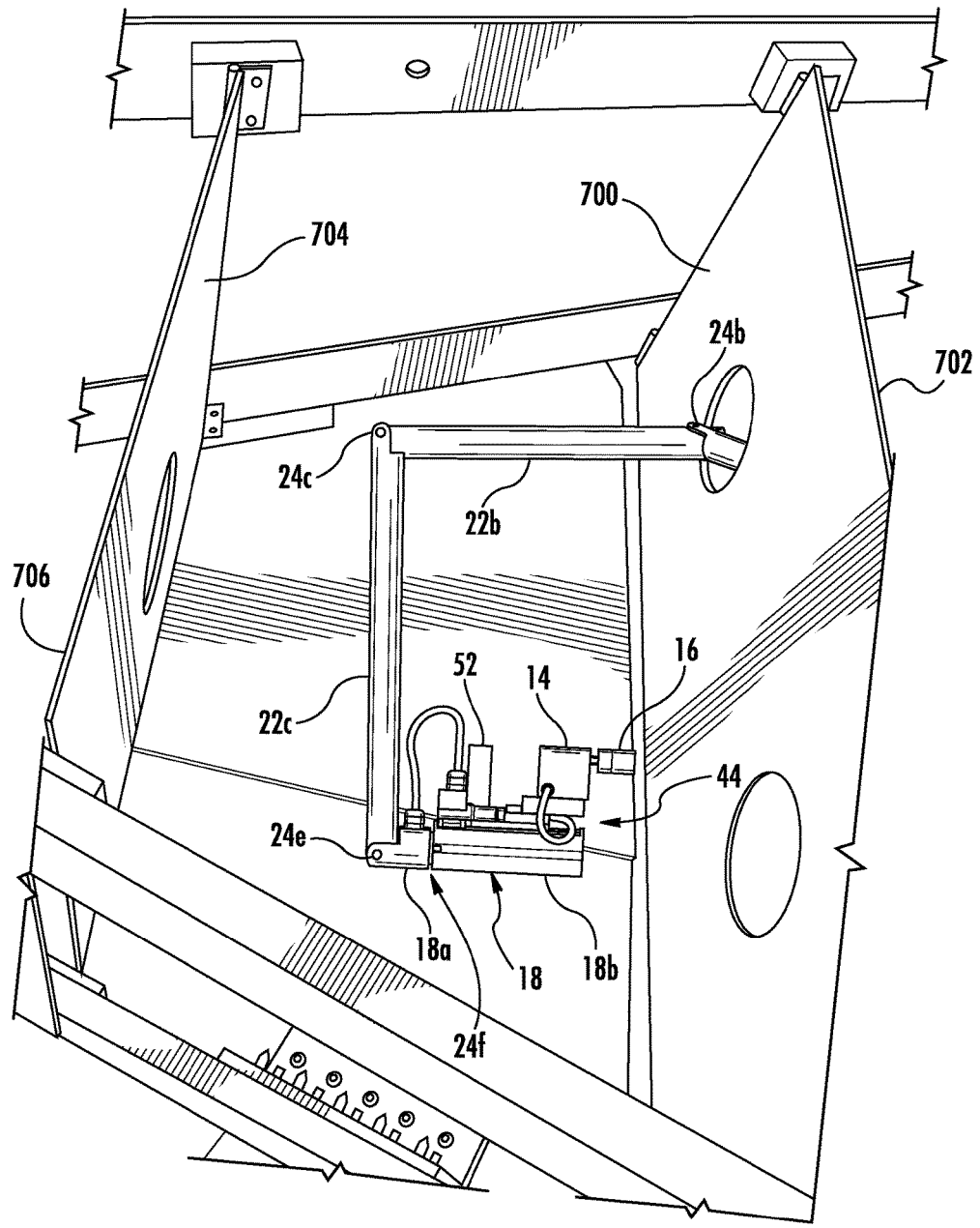
FIG. 7A is a perspective view of the exemplary robotic manipulator arm of FIG. 1 arranged in a first configuration for inspecting elements of a back side of a spar in accordance with an embodiment of the present disclosure.
Figure 7B:
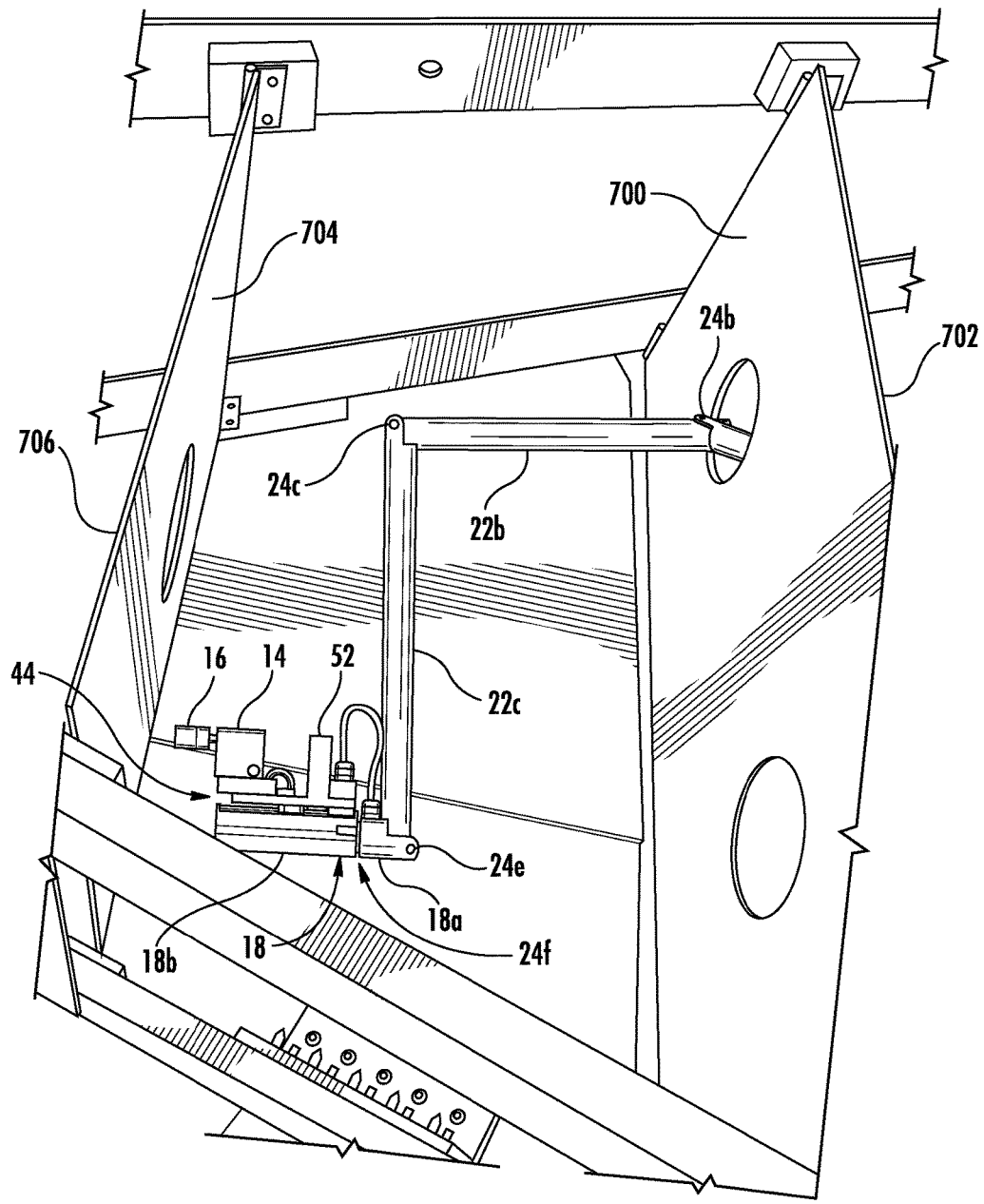
FIG. 7B is a perspective view of the exemplary robotic manipulator arm of FIG. 1 arranged in a second configuration for inspecting elements of a front side of a spar in accordance with an embodiment of the present disclosure.

NDE inspection device. The probe 16 may include, for example, an eddy current sensor, a magnetic sensor, an ultrasonic sensor, or other NDI/NDE type sensor. The robotic manipulator arm 12 may include a plurality of arm segments 18-22. In the example robotic manipulator arm 12 shown in FIG. 1, the plurality of arm segments may include a distal end arm segment 18, a proximal end arm segment 20 and one or more intermediate arm segments 22a, 22b and 22c. The exemplary robotic manipulator arm 12 shown in FIG. 1 includes three intermediate arm segments 22a-22c. Other embodiments may include more or less intermediate arm segments depending on the application or environment. The arm segments 18-22c may be coupled to one another by multi-axis movable joints 24a, 24b, 24c, 24d and 24e. The multi-axis movable joints 24a-24e allow the arm segments 18-22c to be articulated relative to one another as illustrated in FIGS. 7A and 7B. Each multi-axis movable joint 24a-24e may permit the respectively coupled arm segments 18-22c to be positioned at different angles relative to one another. The multi-axis movable joints 24a-24e may also permit the coupled arm segments 18-22c to be rotated relative to one another. For example, multi-axis movable joint 24a may be a universal joint or U-joint that allows the angle of the robotic manipulator arm 12 to differ a certain number of degrees from the proximal end arm segment 20 that is releasably attachable to an access hole or port as described with reference to FIG. 4. Multi-axis joints 24b and 24c may each be a motorized elbow joint that may permit the respectively joined arm segments to be positioned at different angles between about 0 degrees and about 90 degrees. Joint 24d may be a rotating joint that rotates arm segment 22c at different angles between about 0 degrees and about 180 degrees clockwise or counterclockwise about a longitudinal axis 19 that may be defined through the robotic manipulator arm 12 as illustrated in FIG. 1 with all arm segments 22a-22c extending linearly. Multi-axis joint 24e may be motorized elbow joint that may permit the distal end arm segment 18 to be positioned at different angles between about 0 degrees and about 90 degrees relative to the arm segment 22c.

Figure 4:
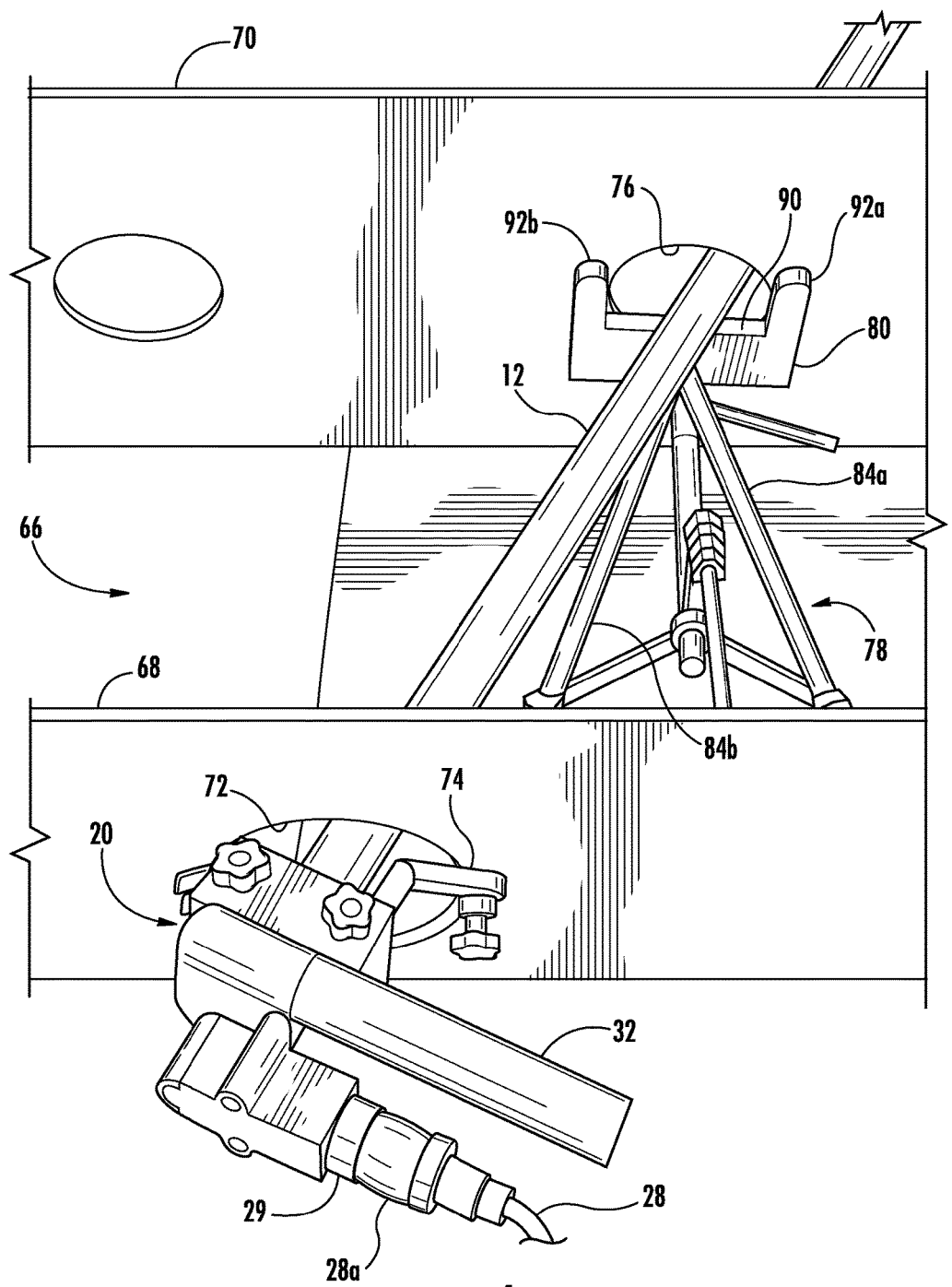
FIG. 4 is a perspective view of an exposed portion of an interior of an enclosed structure illustrating application of the exemplary robotic manipulator arm of FIG. 1.

The movable joints 24a-24e may be motorized joints and may be remotely controlled by a controller 26. An electrical cable 28 may operatively connect the controller 26 to the proximal end arm segment 20 of the robotic manipulator arm 12 to supply electrical power and control operation of the robotic manipulator arm 12. The electrical cable 28 may include electrical power wiring and control wiring for each of the movable joints 24a-24e. The electrical cable 28 may also include signal wiring for controlling operation of the scanner device 14 and for transmitting electrical signals to and from the scanner in response to performing an inspection by the inspection probe 16 on a target or component similar to that described herein. Electrical power wiring and signal wiring may extend through an interior of the robotic manipulator arm 12 for controlling operation of the movable joints 24a-24e and the scanner device 14 and for transmitting signals responsive to the inspection tests. An end of electrical cable 28 may include a suitable plug 28a as best shown in FIG. 4 that may be plugged into a matting receptacle 29 on the proximal end arm segment 20.

The controller 26 may include a plurality of control devices or manipulators 30a, 30b, 30c, etc., such as rotatable dials, joy sticks or other types of control devices, for controlling the movable joints 24a-24e for articulating and rotating the arm segments 18-22c for positioning the scanner device 14 and inspection probe 16 for inspection of a component or target as described herein.

The robotic manipulator arm 12 may also include a control handle 32 coupled to the proximal end arm segment 20 for manipulating the robotic manipulation arm 12. The control handle 32 may be used by an operator for positioning and adjusting placement of the robotic manipulator arm 12 for performing inspections.

The NDI/NDE system 10 may also include a probe camera monitor 34. As described in more detail herein with reference to FIG. 8, a probe camera 36 may be associated with the scanner device 14 for positioning the inspection probe 16 relative to a component or target for inspection. The probe camera 36 may be video camera. The probe camera 36 may be incorporated within the scanner device 14 or may be an integral component of the scanner device 14 as illustrated by the probe camera 36 being shown by a broken line in FIG. 1. Images from the probe camera 36 may be viewed on the probe camera monitor 34 for manipulating the robotic manipulation arm 12 for positioning the inspection probe 16 relative to a target or component for inspection. A centerline of the probe camera 36 is parallel to a centerline of the probe 16 but offset a preset distance. The probe camera 36 may then be disposed directly over a target or component being inspected, such as a fastener connecting parts of an aircraft wing or other parts as viewed by an operator on the probe camera monitor 34. The robotic manipulator arm 12 may then be adjusted the preset distance in a predetermined direction to directly center the inspection probe 16 over the fastener for inspecting the fastener and an area around a circumference of the fastener.

NDI/NDE system 10 may also include a wide angle camera 38 and a wide angle camera monitor 40. The wide angle camera 38 may be coupled to an articulating arm 42. The articulating arm 42 may position the wide angle camera 38 for use in configuring the robotic manipulator arm 12 for inspection of a component or target.

The distal end arm segment 18 may include a stationary portion 18a and rotatable portion 18b that is rotationally coupled to the stationary portion 18a. The longitudinal axis 19 may be defined through the stationary portion 18a and the rotatable portion 18b. The rotatable portion 18b is rotatable about the longitudinal axis 19 relative to the stationary portion 18a. A motorized rotation joint 24f may rotate the rotatable portion 18b between about 0 degrees and about 180 degrees clockwise or counterclockwise relative to the stationary portion 18a. The motorized rotation joint 24f may be remotely controlled by the controller 26.

Figure 2A:
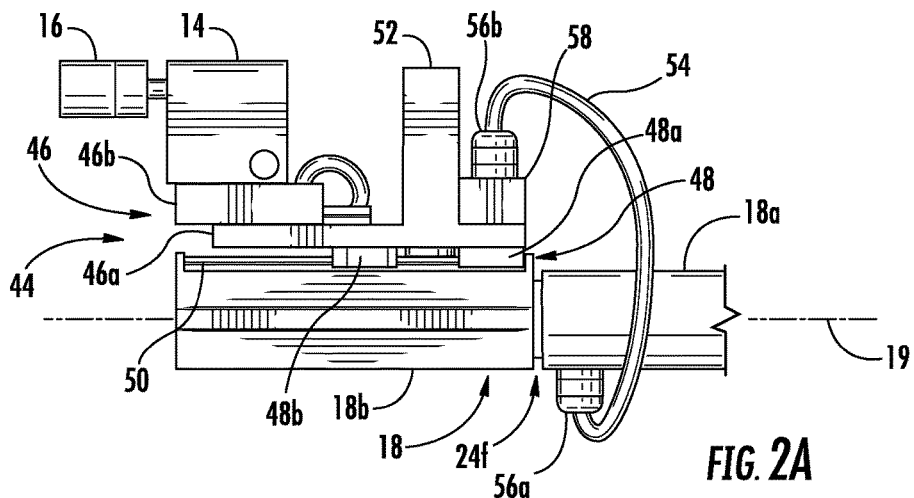
FIG. 2A is a side view of the scanner device mounted to a telescoping extension mechanism of the exemplary robotic manipulator arm with the telescoping extension mechanism in a retracted position in accordance with an embodiment of the present disclosure.
Figure 2B:
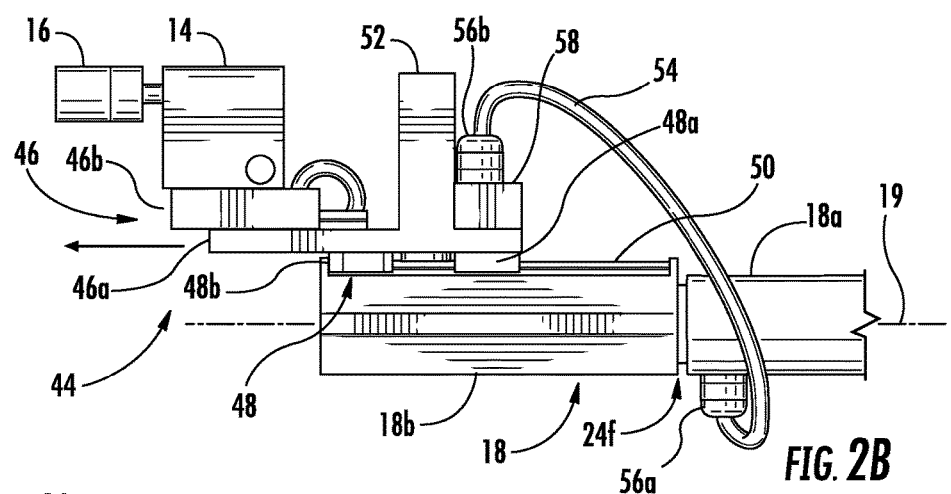
FIG. 2B is a side view of the scanner device mounted to the telescoping extension mechanism of the exemplary robotic manipulator arm with the telescoping extension mechanism in an extended position and a spring biased portion of the base platform in an uncompressed position in accordance with an embodiment of the present disclosure.
Figure 2C:
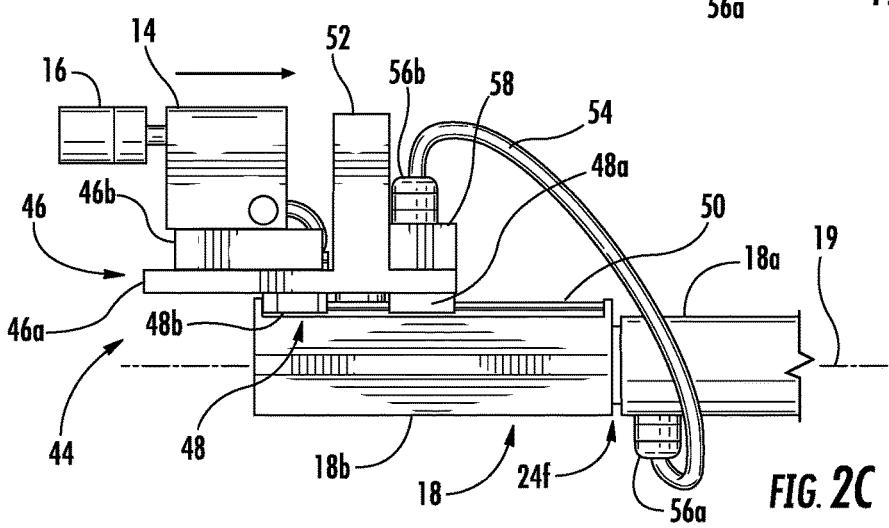
FIG. 2C is a side view of the scanner device mounted to the telescoping extension mechanism of the exemplary robotic manipulator arm with the telescoping extension mechanism in the extended position and spring biased portion of the base platform in a fully compressed position in accordance with an embodiment of the present disclosure.

The robotic manipulator arm 12 may also include a telescoping extension mechanism 44 coupled to the distal end arm segment 18 of the robotic manipulator arm 12. The telescoping extension mechanism 44 may be attached to the rotatable portion 18b of the distal end arm segment 18. The scanner device 14 is mounted to the telescoping extension mechanism 44 for moving the scanner device 14 between a retracted position proximate the robotic manipulator arm 12 and an extended position at a distance from the robotic manipulator arm 12 for performing an inspection similar to that described herein. Referring also to FIGS. 2A-2C, FIG. 2A is a side view of the scanner device 14 mounted to the telescoping extension mechanism 44 of the exemplary robotic manipulator arm 12 with the telescoping extension mechanism 44 in a retracted position in accordance with an embodiment of the present disclosure. FIG. 2B is a side view of the scanner device 14 with the telescoping extension mechanism 44 in an extended position. The telescoping extension mechanism 44 may include a base platform 46. The scanner device 14 may be coupled to one side of the base platform 46. The base platform 46 may include a stationary portion 46a and a spring biased portion 46b. The spring biased portion 46b may be configured to slide relative to the stationary portion 46a and resiliently compress as illustrated in FIG. 2C when the inspection probe 16 is in contact with a component or target during an inspection to maintain contact between the inspection probe 16 and the component when performing an inspection.

A track follower 48 is mounted to an opposite side of the base platform 46. The scanner device 14 may be attached to the spring biased portion 46b of the base platform 46 and the track follower 48 may be mounted to the stationary portion 46a of the base platform 46. The track follower 48 may include a first segment 48a and a second segment 48b. A telescope extension track 50 is mounted to the rotatable portion 18b of the distal end arm segment 18 of the robotic manipulator arm 12. The track follower 48 is configured to move along the telescope extension track 50 between the retracted position and the extended position.

The telescoping extension mechanism 44 also includes a motor 52 that moves the track follower 48 along the telescope extension track 50. The motor 52 may be mounted to the stationary portion 46a of the base platform 46 at a predetermined distance from the spring biased portion 46b to permit compression of the spring biased portion 46b when the inspection probe 16 is in contact with a component or target for performing an inspection. The controller 26 (FIG. 1) may control the motor 52 to move the scanner device 14 between the retracted position as shown in FIG. 2A and the extended position as shown in FIG. 2B. The motor 52 may drive a wheel, a gear or other arrangement (not shown in FIGS. 2A-2B) that may engage the telescope extension track 50 for moving the scanner device 14 between the retracted position and the extended position. For example, the telescope extension track 50 may include a rack gear and the motor 52 may drive a pinion gear for moving the scanner device 14 between the positions.

An electrical cable 54 may be connected between the stationary portion 18a of the distal end arm segment 18 and the telescoping extension mechanism 44 and the rotatable portion 18b of the distal end arm segment 18. The electrical cable 54 may include a first plug 56a that connects to electrical wiring in the stationary portion 18a of the distal end arm segment 18. As previously described, electrical power wiring and signal wiring may extend through the interior of the robotic manipulator arm 12 for controlling operation of the scanner device 14, telescoping extension mechanism 44 and multi-axis movable joints 24a-24f. The electrical cable 54 may also include a second plug 56b for electrically connecting to a receptacle 58 on the stationary portion 46a of the base platform 46 adjacent to the motor 52. The electrical cable 54 is of a sufficient length to allow the rotatable portion 18b of the distal end arm segment 18 to rotate a predetermined angle of rotation relative to the stationary portion 18a and for the telescope extension mechanism 44 to extend to the extended position. For example, the rotatable portion 18b may be rotated between about 0 degrees and at least about 180 degrees clockwise and counterclockwise relative to the stationary portion 18a.

Figure 3A:
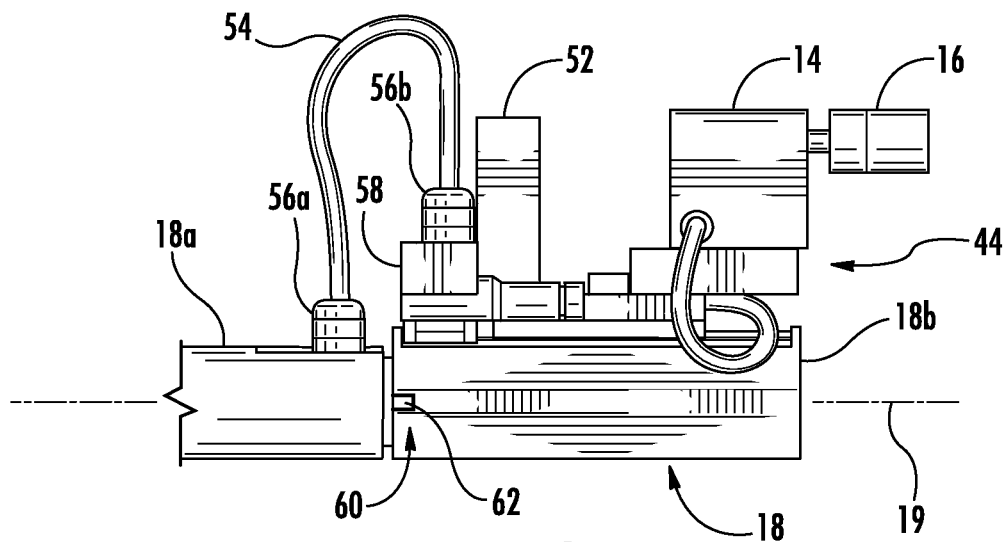
FIG. 3A is a side view of the distal end arm segment of the exemplary robotic manipulator arm showing a first index mark on a rotatable portion of the distal end arm segment for positioning the distal end arm segment in a home position in accordance with an embodiment of the present disclosure.
Figure 3B:
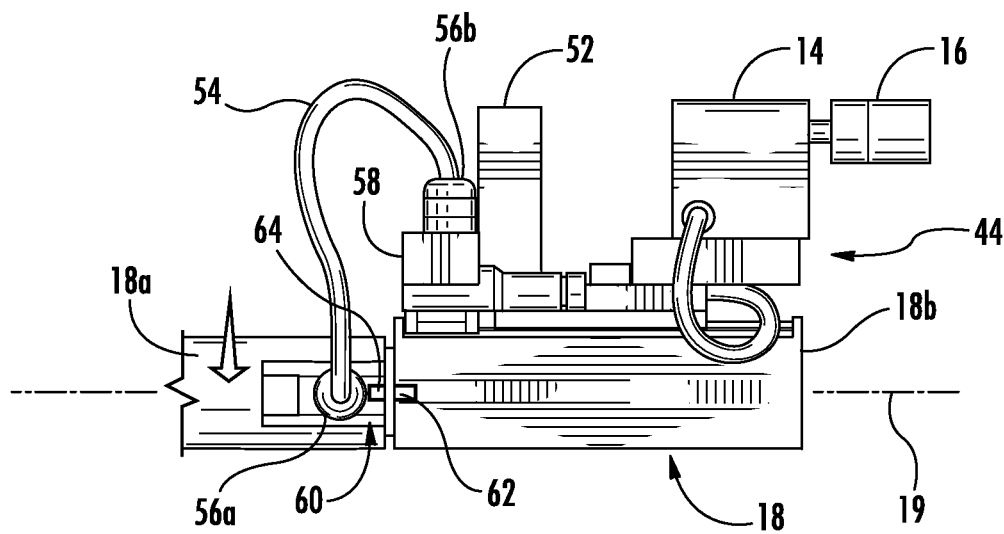
FIG. 3B is a side view of the distal end arm segment of the exemplary robotic manipulator arm showing the first index mark on the rotatable portion and a second index mark on a stationary portion of the distal end arm segment being aligned for positioning the rotatable portion in about a 90 degree position with respect to the stationary portion in accordance with an embodiment of the present disclosure.

Referring also to FIGS. 3A and 3B, the extended reach inspection apparatus 11 may include an indexing feature 60 for determining an angle of rotation of the rotatable portion 18b of the distal end arm segment 18 relative to the stationary portion 18a. FIG. 3A is a side view of the distal end arm segment 18 showing a first index mark 62 at a predetermined location on the rotatable portion 18b of the distal end arm segment 18 for positioning the distal end arm segment 18 in a home position in accordance with an embodiment of the present disclosure. FIG. 3B is a side view of the distal end arm segment 18 showing the first index mark 62 aligned with a second index mark 64 at a predetermine location on the stationary portion 18a for positioning the rotatable portion 18b in a 90 degree position with respect to the stationary portion 18a in accordance with an embodiment of the present disclosure. Accordingly, the rotatable portion 18b is at a first angle of rotation relative to the stationary portion 18a when the first index mark 62 and the second index mark 64 are aligned and the rotatable portion 18b is at a second angle of rotation relative to the stationary portion 18a, for example 90 degrees, when the first index mark 62 and the second index mark 64 are not aligned.

FIG. 4 is a perspective view of an exposed portion of an interior of an enclosed structure 66 illustrating application of the exemplary robotic manipulator arm 12 of FIG. 1. The enclosed structure 66 may be an interior portion of an aircraft, such as a wing or other flight control surface that has limited accessibility except through inspection ports or holes. For example, the enclosed structure 66 may be a midspan of a wing or other portion of an aircraft between a first spar 68 and second spar 70. The robotic manipulator arm 12 may be extended through a first access hole or port 72 in the first spar 68 into the enclosed structure 66. The access hole or port 72 is large enough for the distal end arm segment 18 of the robotic manipulator arm 12 and the scanner device 14 to pass through. In one embodiment the access hole or port 72 may be approximately five inches in diameter. A support bracket 74 may be mounted in the opening 72 to support the proximal end arm segment 20 of the robotic manipulator arm 12.

Figure 5:
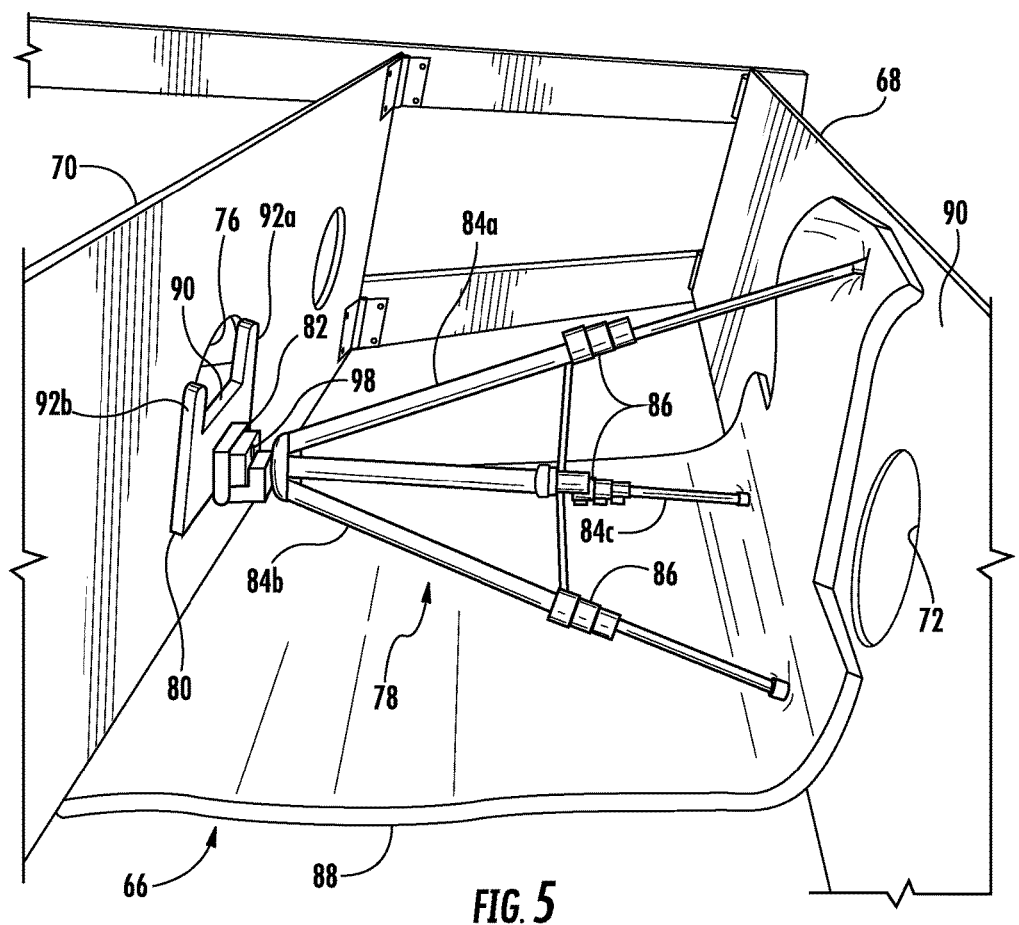
FIG. 5 is a perspective view of an exposed portion of an interior of an enclosed structure between the two spars showing an example of a midspar support apparatus in accordance with an embodiment of the present disclosure.

The robotic manipulator arm 12 may also be extended through at least a second access hole or inspection access port 76 in the second spar 70. A midspar support apparatus 78 may be inserted and deployed in the enclosed structure 66 between the first spar 68 and the second spar 70 to support the robotic manipulator arm 12. Referring also to FIG. 5, FIG. 5 is a perspective view of the exposed portion of the interior of the enclosed structure 66 of FIG. 4 between the two spars 68 and 70 showing an example of the midspar support apparatus 78 in accordance with an embodiment of the present disclosure. An inspection port support member 80 may be releasably attached to the second inspection access port 76 in the second spar 70 to support the robotic manipulator arm 12 extending through the second inspection access port 76. The inspection port support member 80 may protect the second inspection access port 76 and second spar 70 from damage. An example of the inspection port support member 80 will be described in more detail with reference to FIGS. 6A and 6B. The midspar support apparatus 78 may include a head fitting 82 configured to releasably attach to the inspection port support member 80 that is releasable attachable to the inspection access port 76 in the second spar 70. The midspar support apparatus 78 may also include a plurality of collapsible leg members 84a, 84b and 84c extending from the head fitting 82. The plurality of collapsible leg members 84a, 84b and 84c may be configured to contact the first spar 68 opposite the second spar 70. The plurality of collapsible leg member 84a, 84b and 84c may each be adjustable in length and may each include a locking mechanism 86 to retain each leg at a selected length. The plurality of collapsible leg members 84a, 84b and 84c may be collapsible to fit through the first inspection access port 72 in the in the first spar 68.

A protective pad 88 may be disposed between the first spar 68 and the second spar 70. The protective pad 88 may also be extendable over a face 90 of the first spar 68. The protective pad 88 protects the interior area of the enclosed structure 66 between the first spar 68 and the second spar 78 and the face of the first spar 68 from damage during installation and removal of the midspar support apparatus 78 and the robotic manipulator arm 12 during an inspection procedure. For an interior area that is within an aircraft, aircraft components, such as wings and other flight control surfaces may be manufactured from a lightweight honeycomb sandwich structure including a cellular layer including a multiplicity of honeycomb shaped cells disposed or sandwiched between an inner layer of material and outer layer of material. The honeycomb sandwich structure may be damaged if impacted by the robotic manipulator arm 12 or midspar support apparatus 78.

Figure 6A:
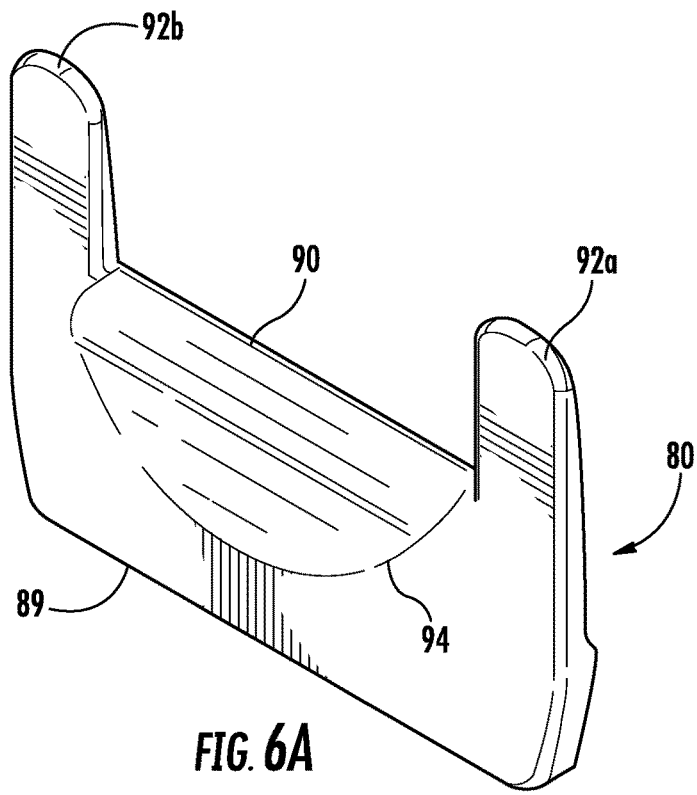
FIG. 6A is a perspective view of a back side of an example of an inspection port support member for use with a midspar support apparatus in accordance an embodiment of the present disclosure.
Figure 6B:
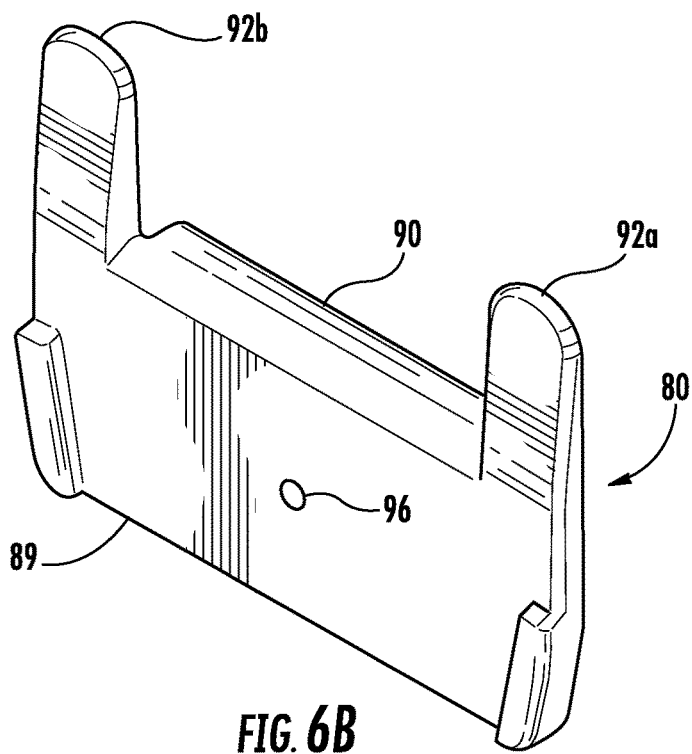
FIG. 6B is a perspective view of a front side of the exemplary inspection port support member of FIG. 6A.

Referring also to FIGS. 6A and 6B, FIG. 6A is a perspective view of a back side of an example of the inspection port support member 80 for use with the midspar support apparatus 78 in accordance an embodiment of the present disclosure. FIG. 6B is a perspective view of a front side of the inspection port support member 80 of FIG. 6A. The inspection port support member 80 may include a substantially rectangular shaped main body 89 with a flat top portion 90 to extend across the inspection access port 76 as shown in FIGS. 4 and 5. The robotic manipulator arm 12 may rest on the flat top portion 90 and slide along the flat top portion 90 between appendages 92a and 92b during an inspection procedure. Appendage 92a and 92a may extend from the main body 89 at opposite ends of the flat top portion 90. The appendages 92a and 92b may prevent the robotic manipulator arm 12 from striking an interior the inspection access port 76 opening and causing damage when the robotic manipulator arm 12 moved or positioned for performing an inspection.

The inspection port support member 80 may also include a substantially semi-circular shaped lip 94 extending from the flat top portion 90 (FIG. 6A). The semi-circular shaped lip 94 is configured to matingly contact or releasably attach to an interior lower edge of the second inspection access port 76. The semi-circular lip 94 may have an upside down J-shape or may be hook shaped to releasably attach to or hang over the interior lower edge of the second inspection access port 76.

The inspection port support member 80 may also include a threaded opening 96. The threaded opening 96 may be configured to matingly receive a screw 98 (FIG. 5) captured by the head fitting 82 for attaching the inspection support member 80 to the midspar support apparatus 78.

FIG. 7A is a perspective view of the exemplary robotic manipulator arm 12 of FIG. 1 arranged in a first configuration for inspecting elements of a back side 700 of a spar 702 in accordance with an embodiment of the present disclosure. FIG. 7B is a perspective view of the exemplary robotic manipulator arm 12 of FIG. 1 arranged in a second configuration for inspecting elements of a front side 704 of a second spar 706 in accordance with an embodiment of the present disclosure. As illustrated in FIGS. 7A and 7B, the distal end arm segment 18 and the intermediate arm segments 22b and 22c may be articulated by the multi-axis movable joints 24b, 24c and 24d for inspecting different components or targets within an enclosed structure, such as an interior or an aircraft wing or other structure.

Figure 8:
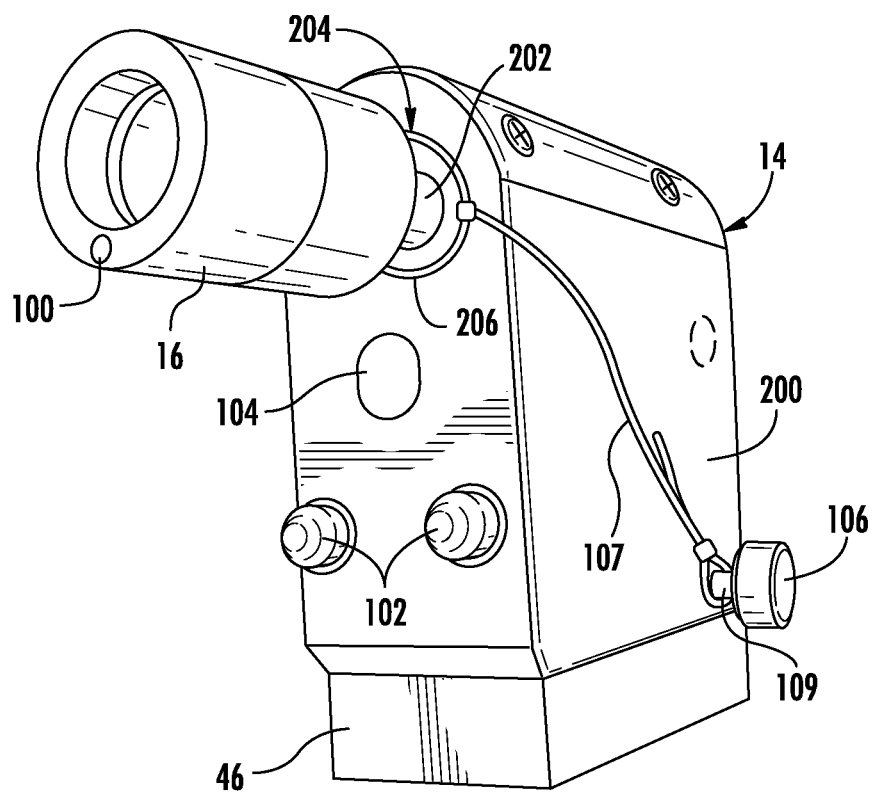
FIG. 8 is a front end perspective view of an example of a scanner device including a probe in accordance with an embodiment of the present disclosure.
Figure 9:
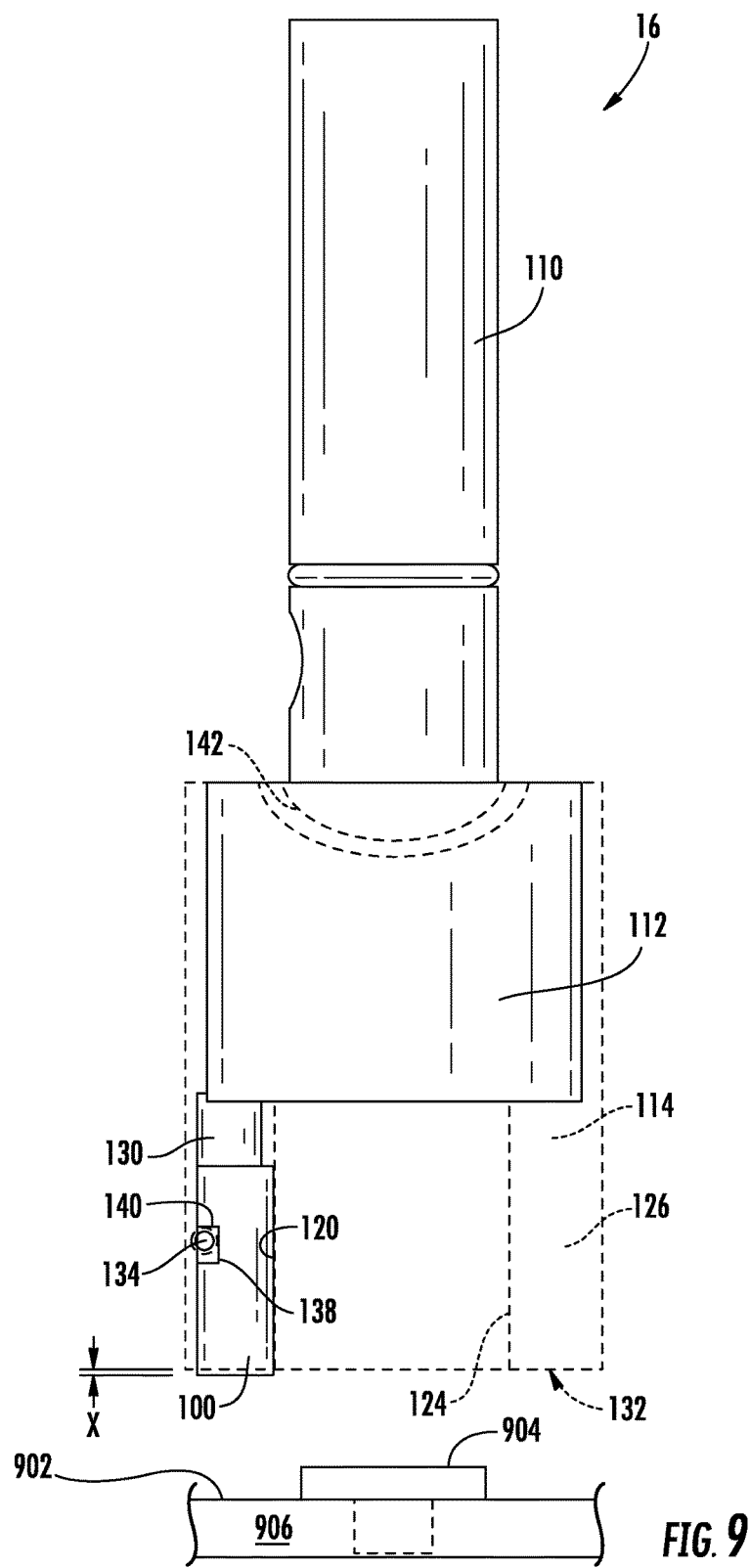
FIG. 9 is a side view of an example of a probe in accordance with an embodiment of the present disclosure.
Figure 10:
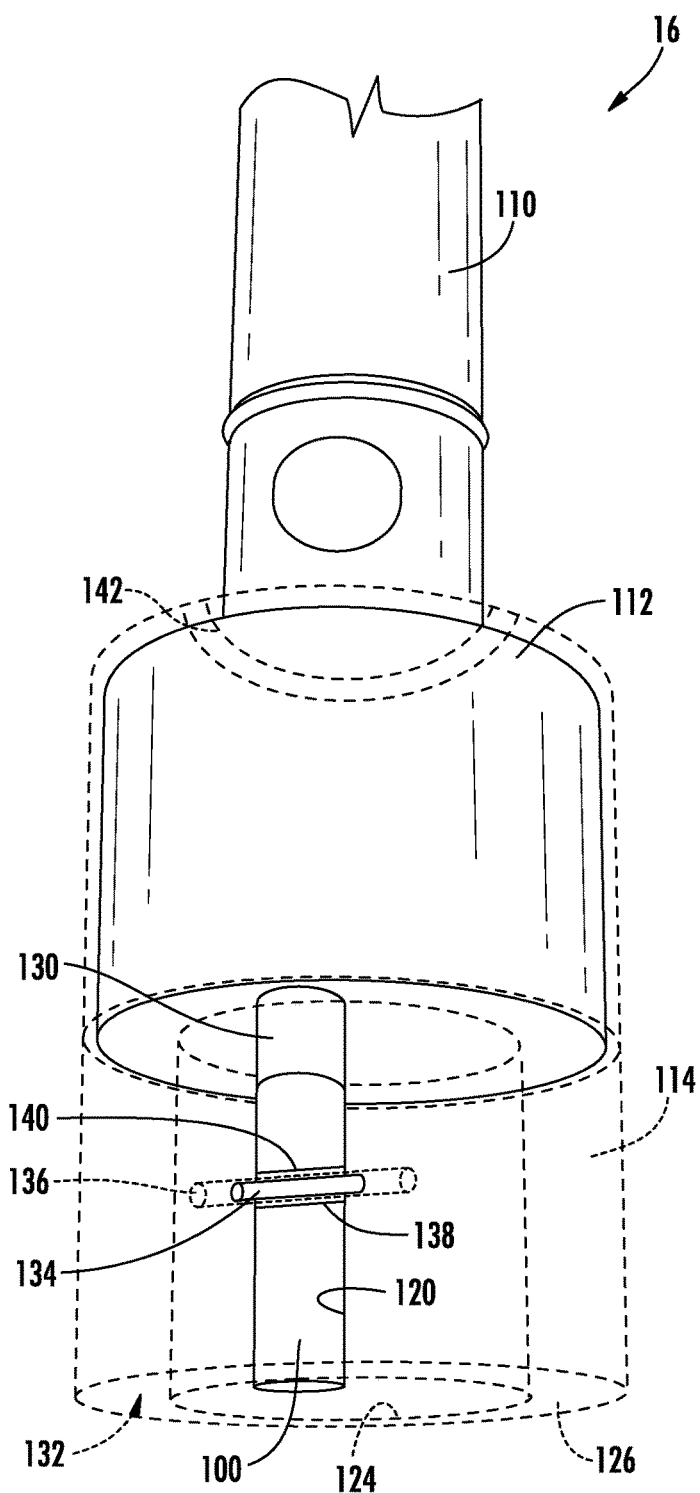
FIG. 10 is a side perspective view of the exemplary probe of FIG. 9.

FIG. 8 is an end perspective view of the scanner device 14, which includes an embodiment of an inspection probe 16 mounted to the scanner device 14. In this embodiment, the inspection probe 16 may include an eddy current sensor 100, including a coil of wire. The scanner device 14 may be a micro eddy current rotating scanner, which may include a motor. It is not necessary for other embodiments of the system 10 (FIG. 1) or the inspection probe 16 that the scanner device 14 be a rotating type. The distal end of the scanner device 14 may include lights 102, for example LEDs, to illuminate the enclosure and the target to be inspected, and a camera lens 104 to provide an image to the probe camera 36 (FIG. 1) in the scanner device 14. Another video camera could also be mounted in proximity of the inspection probe 16 to provide additional situational awareness. A knob 106 has a threaded bolt 109 on it that may be loosened to remove the scanner device 14 from the base platform 46 of the telescoping extension mechanism 44 (FIGS. 1-2C). The other end of the threaded bolt 109 may bear against a cylinder (not shown in FIG. 8) to which the scanner device 14 is attached.

A tether 107 may be looped around the threaded bolt 109 of the knob 106 and another end of the tether 107 may be secured to the inspection probe 16. The scanner device 14 may include a scanner body 200. The inspection probe 16 may extend from the scanner body 200 on a rotating shaft 202 or spindle. The inspection probe 16 is removable from the scanner device 14 and may be dislodged from the scanner body 200 if the inspection probe 16 strikes an object during insertion or removal of the robotic manipulator arm 12 during an inspection procedure. The tether 107 connects the probe 16 to the scanner body 200 to prevent loss of the probe within an interior of a structure under inspection. The tether 107 will retain the inspection probe 16 with the scanner body 200 in response to the inspection probe 16 being pulled from the scanner device 14. In accordance with an embodiment, a collar 204 may be attached to the shaft 202. The collar 204 may include a groove 206 for receiving and retaining the tether 107. The tether 107 may be looped around the groove 206 in the collar 107 and fastened to retain the tether 107 within the groove 206. In another embodiment, the collar 107 may be a bearing fastened to the shaft 202 with a groove in an exterior portion of the bearing. The bearing allows the shaft 202 to rotate within the bearing and the tether 107 fastened within the groove in the exterior portion of the bearing is allowed free movement or to remain stationary as the shaft 202 rotates during performance of an inspection.

Figure 11:
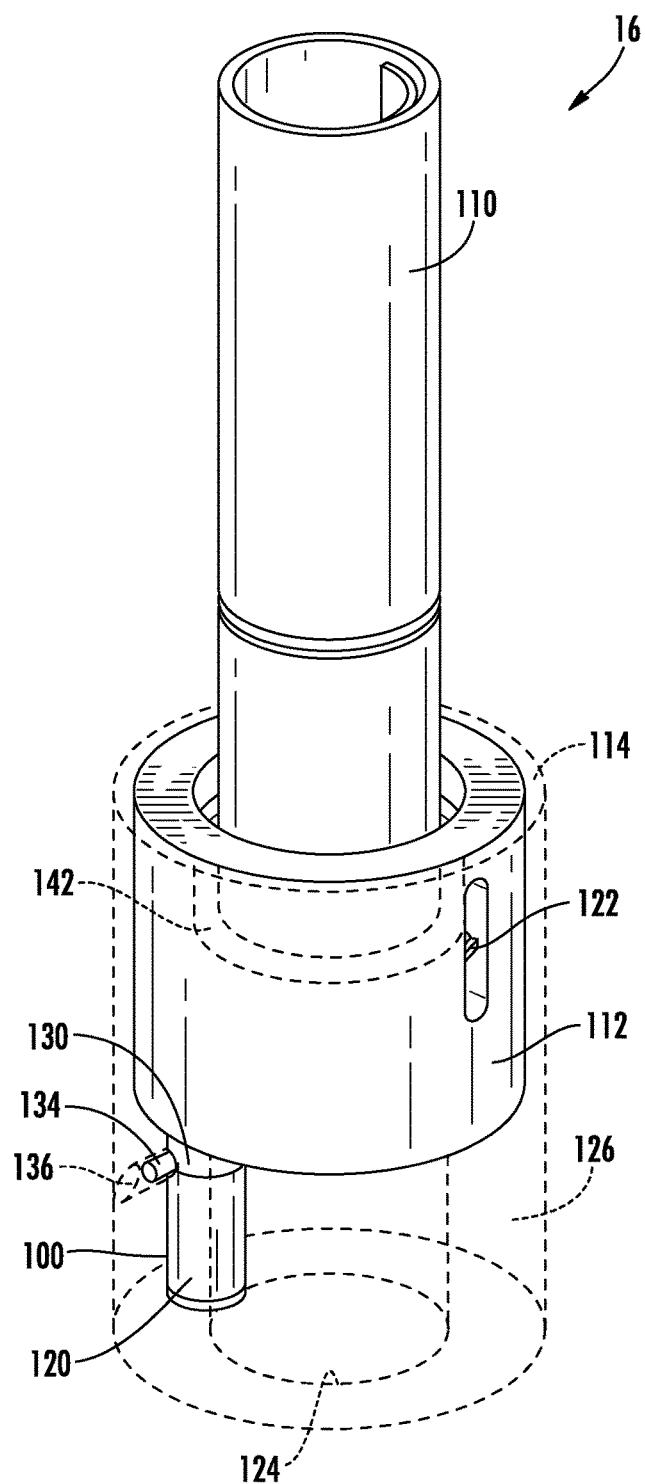
FIG. 11 is another side perspective view of the exemplary probe of FIG. 9.
Figure 12:
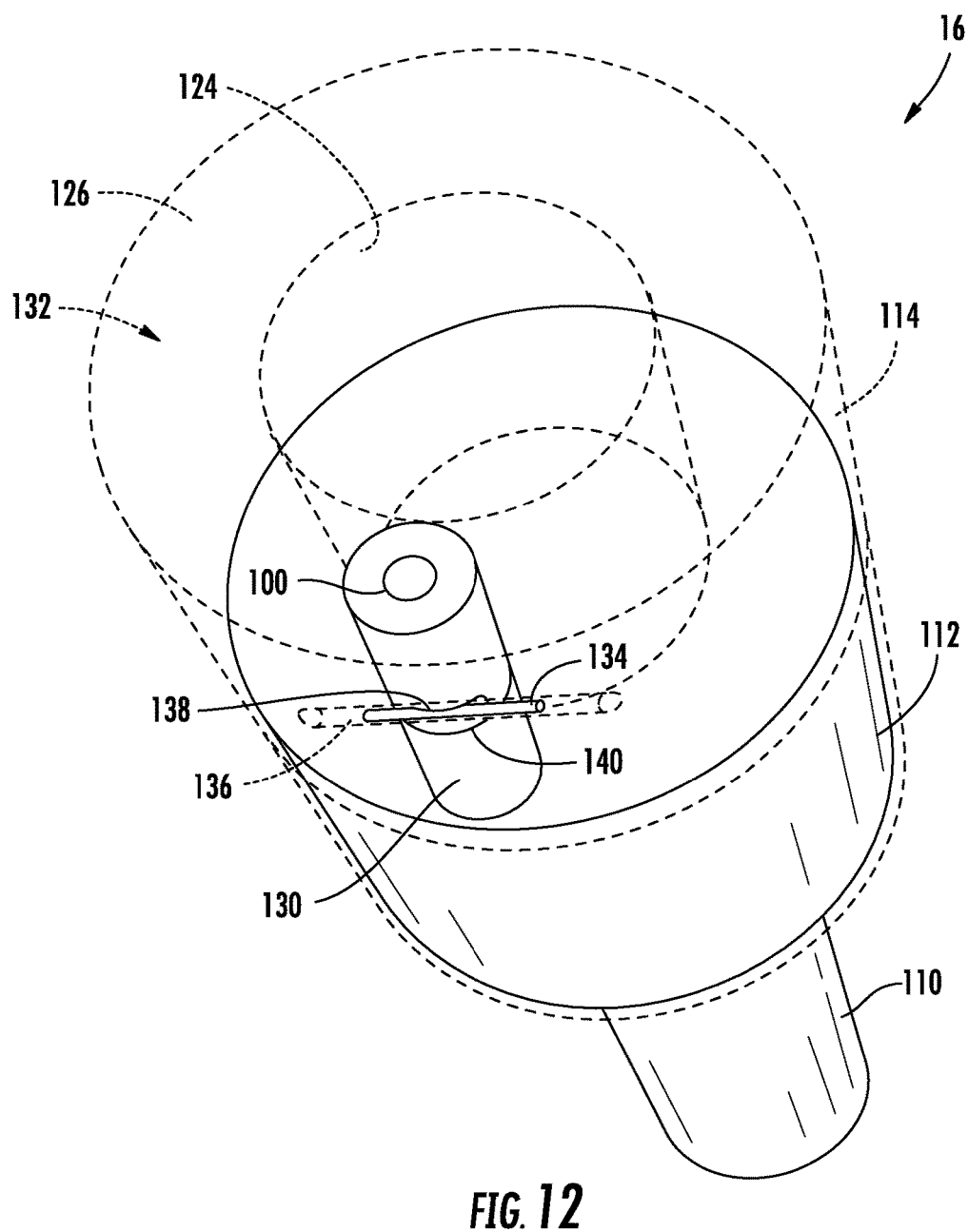
FIG. 12 is a bottom perspective view of the exemplary probe of FIG. 9.

FIGS. 9-12 show an embodiment of the inspection probe 16 with an embodiment of an eddy current sensor 100. The inspection probe 16 may include a spindle 110, a central member 112 mounted to the spindle 110, and a housing 114 mounted to the central member 112. In this embodiment, the housing 114 is translucent. The sensor 100 may be received in an opening which may be a bore 120 in the housing 114 or be otherwise slidably mounted to the housing 114. The central member 112 may be mounted to the spindle 110 with a set screw 122 (FIG. 11). The housing 114 may be cylindrical, may encase the sides of the central member 112, and extends distally below the bottom of the central member 112. Below the distal end of the central member 112 the housing 114 may define a substantially cylindrical opening 124 and have a cylindrical wall 126. The cylindrical wall 126 may be of adequate thickness to receive the sensor 100 in the bore 120 in the wall 126, as shown, or other configurations may be provided to attach the sensor 100 to the inspection probe 16. In the example shown in FIG. 9, the inspection probe 16 may be configured for inspecting the metal 902 around a fastener 904 of a component of a structure 906, such as an aircraft wing or other structure. The opening 124 in the housing 114 is large enough to receive the end of the fastener 904 that protrudes from the structure.

A spring 130, such as a coil spring as schematically shown, a leaf spring, compressible and resilient material, or other biasing means may be provided in between the proximal end of the bore 120 and the proximal end of the sensor 110, and urges the sensor 100 distally such that the sensor 100 may extend out of the bore 120 past the distal surface 132 of the housing 114. The spring loading increases the probe's compliance to the surface of the structure 906 under inspection. Seating of the eddy current sensor 100 over the fastener so that the sensor 100 lies as flat as possible on the structure 906 is generally desirable for conducting a proper inspection. The sensor 100 is retained in the bore 120 with a pin 134 that extends laterally through an opening 136 in the housing wall 126 and passes through a slot 138 in the sensor 100. The proximal side 140 of the slot 138 is blocked by the pin 134 as the spring 130 urges the sensor 100 to withdraw from the bore 120. The proximal side 140 of the slot 138 is located such that the sensor 100 may extend a predetermined distance X from the bore 120 below the distal surface 132 of the housing 114.

In addition, a joint 142 may be provided in the spindle 110 at the connection to the central member 112. The joint 142 may be, for example, a gimbal joint, a ball and socket type joint, or the like, and in the embodiment of an inspection probe 16 described herein, may allow for a deflection of, for example, at least approximately 12 degrees, with a preferred angle of at least 15 degrees between the spindle 110 and the longitudinal axis of the inspection probe 16. Joint deflection may be greater with other embodiments, and particularly in embodiments where the sensor 100 can extend a greater predetermined distance X from the bore 120 below the distal surface 132 of the housing 114 than in the exemplary embodiment described herein.

The joint 142 may be designed to transfer scan rotation through an angle as needed, but to return to a zero angle position when the end is free, which may be referred to as self-aligning. This self-aligning may be accomplished in a variety of ways, for example in a ball and socket type joint, using a non-spherical ball and socket that pulls slightly out and extends an inner spring when an angle away from the longitudinal axis of the inspection probe 16 is created. The spindle 110 and joint 142 rotate during scanning, as does the rest of the inspection probe 16.

In one exemplary embodiment, the inside diameter of the housing 114 is 0.5 inches, the housing wall 126 thickness distally from the central member 112 is 0.112 inches, the radius from the longitudinal axis of the inspection probe 16 to the longitudinal axis of the sensor 100 is 0.183 inches, and the predetermined distance X that the sensor 100 may extend past the distal surface 132 of the housing 114 is 0.008 inches.

The probe materials may include, for example, for the central member 112, spindle 110, spring 130, and pin 134, metals such as steel, stainless steel, or other steel alloy. The housing 114 may be molded plastic or other nonconductive material, which may be translucent to facilitate assembly and visualization of a fastener during scanning. The sensor 100 may be made of materials as known to one of ordinary skill in the art.

Figure 13:
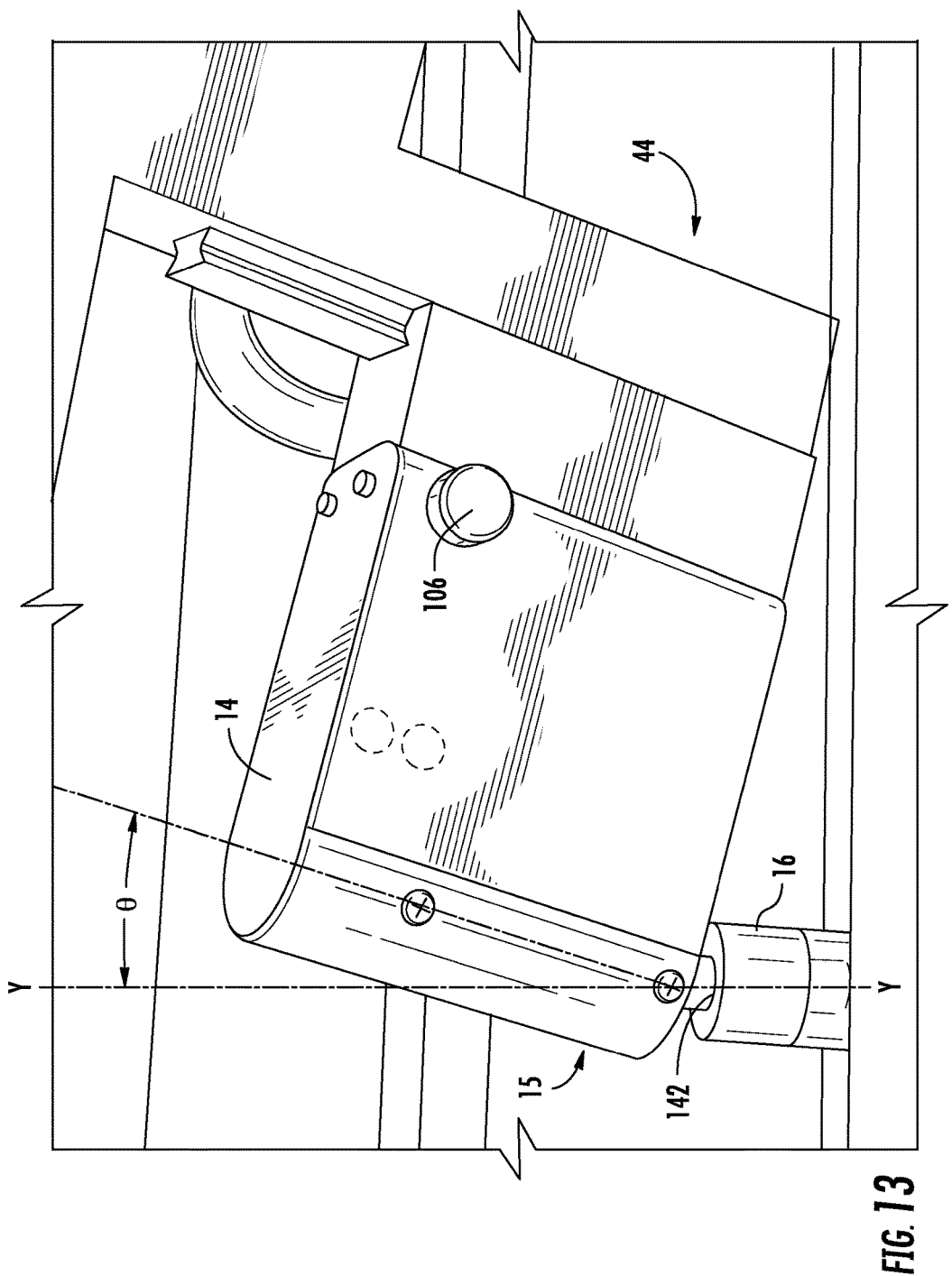
FIG. 13 is a side perspective view of the exemplary scanner device including a probe of FIG. 8.

FIG. 13 shows a detail view of the end effector 15 or scanner device 14 in use. Angle θ is the predetermined deflection angle that the joint 142 provides. As shown, the joint 142 allows a deflection of approximately 15 degrees between the spindle 110 and the longitudinal axis Y-Y of the inspection probe 16. The distance that the sensor 100 can extend past the distal surface 132 of the housing 114 makes this relatively high degree of deflection possible. When the inspection probe 16, and the sensor 100 with it, rotates when the housing 114 is not parallel to the target surface, there will be one point on the path of rotation where the distal surface 132 of the housing 114 is closest to the target, preferably with the sensor 100 touching the target surface, and a point on the opposite side of the path of rotation where the distal surface 132 of the housing 114 is farthest away from the target surface, and without the extension of the sensor 100 lift-off will be experienced. The extending of the sensor 100 past the distal surface 132 of the housing 114 reduces the amount of lift-off or eliminates lift-off, and may keep the sensitivity of the sensor 100 adequate to provide meaningful NDE data over the entire path of rotation. The sensor 100 extending also allows the deflection angle to be increased in the design of the joint 142. An increased available deflection angle facilitates applying and using the inspection probe 16.

Figure 14:
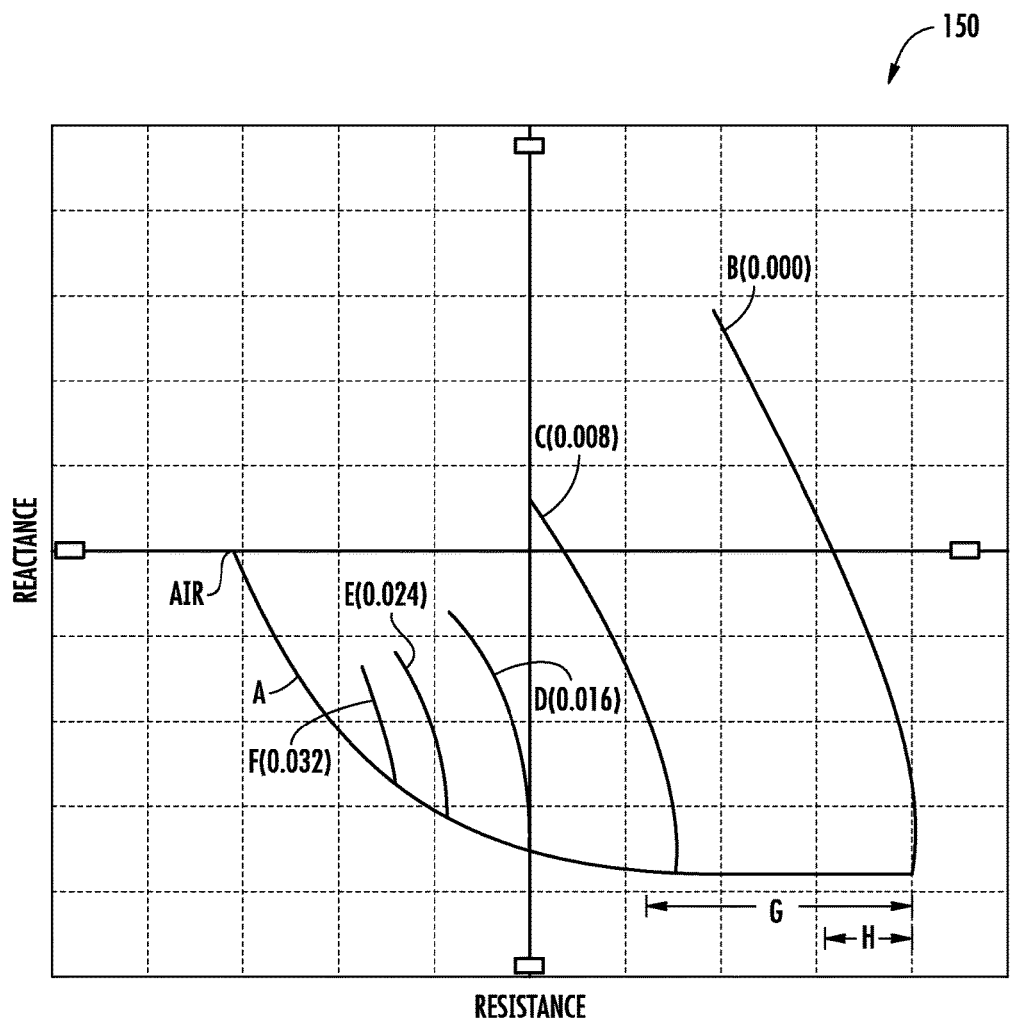
FIG. 14 is an example of a high frequency eddy current impedance plane display that may result from application of the exemplary probe of FIG. 9 in inspecting an aluminum structure in accordance with an embodiment of the present disclosure.

FIG. 14 shows a high frequency eddy current impedance plane display 150 as may result from application of an inspection probe 16 including an eddy current sensor 100 applied to an aluminum structure. This display 150 may aid an operator/inspector in knowing when the inspection probe 16 is coupled to the structure to allow proper inspection. Resistance is plotted on the X-axis and Reactance is plotted on the Y-axis. The eddy current probe is "nulled" in air, which appears on the display 150 at the far left at the label "AIR" where there is no magnetic field measurement, as opposed to the often used technique of nulling the inspection probe 16 while on the part being inspected, and then, as the inspection probe 16 is brought down over the fastener 902, the eddy current display "dot" comes down to the position where the inspection probe 16 is coupled with the part or structure 906.

Curve A in FIG. 14 represents decreasing magnetic field readings from right to left, which corresponds to increased lift-off from right to left. Multiple flaw indications are shown in FIG. 14. These flaw indications are curves B through F, which are each the result of the sensor 100 detecting the same 0.050 inch deep Electrical Discharge Machining (EDM) notch, but with different distances of lift-off. The curves B through F are also labeled with dimensions that designate the distance of lift-off in inches for each of the respective curves. To obtain a desirable 3:1 signal-to-noise ratio (S/N), in testing with the example discussed above in the discussion of FIGS. 9-12, the lift-off of the sensor 100 from the part could not be more than 0.016 inches. Below 0.016 inch lift-off, the inspection probe 16 and structure 906 was considered to be coupled. If the lift-off was greater than this amount, the flaw indication may be detectable, but the S/N was less than desirable and it may become difficult to distinguish a crack in the part from lift-off.

In a test with an eddy current sensor mounted to a probe without a spring to extend the sensor out of the housing, and a spindle with a joint allowing an angle of incidence of 10.5 degrees off of a line perpendicular to the target surface, the dot traveled along curve A approximately within range G as the sensor rotated. With a spring that allowed the sensor to extend 0.008 inches out of the housing, the joint angle could be increased to 15 degrees, and the dot traveled approximately only within range H, providing improved ability to accurately detect flaws.

There are some significant differences between aluminum and titanium structures when eddy current testing for surface flaws. Titanium electrical conductive is significant less than aluminum. This requires a much different coil driver frequency, which generate the eddy currents in the structure, to detect the surface flaw. These driver frequencies in titanium are much higher, which causes the eddy current depth-of-penetration to be significantly less, and detection of the crack more sensitive to different amounts of lift-off, or coil distances lifted-off the surface of the structure.

Figure 15:
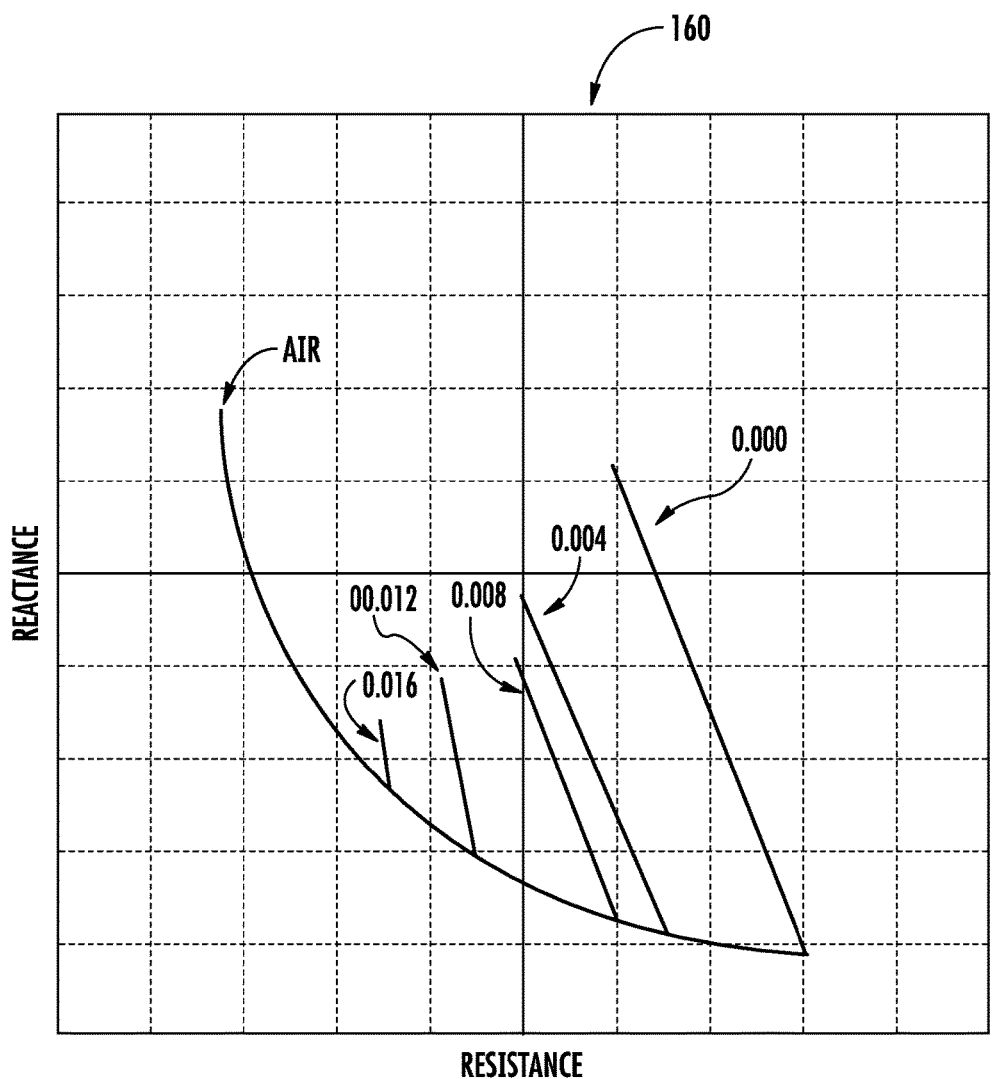
FIG. 15 is an example of a high frequency eddy current impedance plane display that may result from application of the exemplary probe of FIG. 9 in inspecting a titanium structure in accordance with another embodiment of the present disclosure.

FIG. 15 shows a high frequency eddy current impedance plane display 160 as may result from application of an inspection probe 16 including an eddy current sensor 100 applied to a titanium structure. Each of the curves in FIG. 15 are labeled with dimensions that designate the distance of lift-off in inches from a surface of the structure. FIG. 14 shows the flaw amplitude decreasing with increasing amounts of lift-off of the coil for the aluminum structure. FIG. 15 shows the flaw amplitude decreasing with increasing amounts of lift-off of the coil for the titanium structure. As shown in FIG. 14 the amount of lift-off for roughly a 50% decrease in amplitude is 0.016-inches, where in FIG. 15 the amount of lift-off for roughly a 50% decrease in amplitude is 0.008-inches. Also, it can be seen that in aluminum (FIG. 14) that a lift-off of 0.032-inches can still detect the flaw, where with titanium the maximum amount of lift-off to detect the flaw is 0.016-inches.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the embodiments herein have other applications in other environments. This application is intended to cover any adaptations or variations of the present disclosure. The following claims are in no way intended to limit the scope of the disclosure to the specific embodiments described herein.

What is claimed is:

1. An extended reach inspection apparatus (11), comprising:
   a scanner device (14);
   a robotic manipulator arm (12), the robotic manipulator arm comprising:
      a plurality of arm segments (18, 20, 22a-22c) comprising a distal end arm segment (18) and a proximal end arm segment (20), the distal end arm segment comprising:
         a stationary portion (18a) coupled to the robotic manipulator arm by a movable joint;
         a rotatable portion (18b) rotationally coupled to the stationary portion; and
         a longitudinal axis (19) defined through the stationary portion and the rotatable portion, the rotatable portion being rotatable about the longitudinal axis relative to the stationary portion;
      a telescoping extension mechanism (44) coupled to the distal end arm segment, wherein the scanner device is mounted to the telescoping extension mechanism for moving the scanner device between a retracted position proximate the robotic manipulator arm and an extended position at a distance from the robotic manipulator arm, the telescoping extension mechanism being mounted on the rotatable portion of the distal arm segment; and
      a control handle (32) coupled to the proximal end arm segment of the plurality of arm segments for manipulating the robotic manipulator arm.

2. The extended reach inspection apparatus of claim 1, further comprising a controller (26) operatively connected to the robotic manipulator arm (12) for controlling the telescoping extension mechanism (44) to move the scanner device (14) between the retracted position and the elongated position.

3. The extended reach inspection apparatus of claim 2, wherein the telescoping extension mechanism (44) comprises:
   a base platform (46), the scanner device being coupled to one side of the base platform;
   a track follower (48) mounted to an opposite side of the base platform;
   a telescope extension track (50) mounted to the distal end arm segment of the robotic manipulator arm, wherein the track follower is configured to move along the telescope extension track between the retracted position and the extended position; and
   a motor (52) that moves the track follower along the telescope extension track, wherein the controller controls the motor to move the scanner device between the retracted position and the extended position.

4. The extended reach inspection apparatus of claim 3, wherein the telescope extension track comprises a rack gear that engages a pinion gear driven by the motor.

5. The extended reach inspection apparatus of claim 3, wherein the base platform comprises a stationary portion and a spring biased portion, the spring biased portion being configured to slide relative to the stationary portion and resiliently compress when an inspection probe of the scanner device is in contact with a component or target during an inspection to maintain contact between the inspection probe and the component when performing an inspection.

6. The extended reach inspection apparatus of claim 1, further comprising an indexing feature (60) for determining an angle of rotation of the rotatable portion relative to the stationary portion.

7. The extended reach inspection apparatus of claim 6, wherein the indexing feature comprises:
   a first index mark (62) positioned at a predetermined location on the stationary portion;
   a second index mark (64) positioned at a predetermined location on the rotatable portion, wherein the rotatable portion is at a first angle of rotation relative to the stationary portion when the first index mark and the second index mark are aligned and the rotatable portion is at a second angle of rotation relative to the stationary portion when the first index mark and the second index mark are not aligned.

8. The extended reach inspection apparatus of claim 1, wherein the scanner device comprises:
   a scanner body (200);
   a probe (16) extending from the scanner body for inspecting a component, wherein the probe is removable from the scanner device; and
   a tether (107) coupled to the probe and to the scanner body, the tether retaining the probe with the scanner body in response to the probe being pulled from the scanner device.

9. The extended reach inspection apparatus of claim 8, wherein the probe comprises a shaft (202) for rotating the probe by the scanner device to perform an inspection, the extended reach inspection apparatus further comprising a collar (204) attached to the shaft, the collar comprising a groove (206) for receiving and retaining the tether and allowing the shaft to rotate the probe.

10. The extended reach inspection apparatus of claim 1, further comprising an inspection port support member (80), the inspection port support member being releasably attachable to an inspection port (76) and being configured to support the robotic manipulator arm extending through the inspection port.

11. The extended reach inspection apparatus of claim 10, further comprising a midspar support apparatus (78) configured to support the robotic manipulator arm between two spars (68, 70) of an enclosed structure (66), the midspar support apparatus comprising:
   a head fitting (82) configured to releasably attach to the inspection port support member that is releasable attachable to a first inspection port (76) in a first spar (70); and
   a plurality of collapsible leg members (84a-84c) extending from the head fitting, the plurality of collapsible leg members being configured to contact a second spar (68) opposite the first spar, the plurality of collapsible leg members being collapsible to fit through a second inspection port (72) in the second spar.

12. The extended reach inspection apparatus of claim 11, further comprising a protective pad (88) disposable between the first spar and the second spar and extendable over a face (90) of the second spar, the protective pad protecting an interior area of the enclosed structure (66) between the first spar and the second spar and the face of the second spar from damage during installation and removal of the midspar support apparatus and the robotic manipulator arm during an inspection procedure.

13. The extended reach inspection apparatus of claim 1, further comprising:
   a camera (36) associated with the scanner device, wherein the camera is positioned with respect to an inspection probe (16) of the scanner device for positioning the inspection probe relative to a component (904) for inspection of the component; and
   a monitor (34) coupled to the camera for viewing an image of the component to be inspected and the robotic manipulator arm being movable to position the inspection probe relative to the component for inspection of the component.

14. The extended reach inspection apparatus (11) of claim 1, wherein the scanner device comprises:
   a probe (16) having a longitudinal axis, a first end, and a second, free end defining an opening (124), wherein the opening is offset from the longitudinal axis;
   a sensor (100) for inspecting a target and providing an electrical output, the sensor being received in the opening, wherein when the probe is rotated about the longitudinal axis, the sensor moves in a substantially circular path; and
   bias means (130) received in the opening in between the first end of the probe and the sensor to urge the sensor away from the first end of the probe.

15. The extended reach inspection apparatus of claim 14, further comprising a midspar support apparatus (78) configured to support the robotic manipulator arm between two spars (68, 70) of an enclosed structure (66), the midspar support apparatus comprising:
   an inspection port support member (80) configured to releasable attach to a first inspection port (76) in a first spar (70); and
   a plurality of collapsible leg members (84a-84c) extending from the inspection port support member, the plurality of collapsible leg members being configured to contact a second spar (68) opposite the first spar, the plurality of collapsible leg members being collapsible to fit through a second inspection port (72) in the second spar.

16. The extended reach inspection apparatus of claim 14, a camera (36) associated with the scanner device, wherein the camera is positioned with respect to an inspection probe (16) of the scanner device for positioning the inspection probe relative to a component (904) for inspection of the component; and
   a monitor (34) coupled to the camera for viewing an image of the component to be inspected and the robotic manipulator arm being movable to position the inspection probe relative to the component for inspection of the component.

17. The extended reach inspection apparatus of claim 14, wherein the probe comprises a shaft (202) for rotating the probe by the scanner device to perform an inspection, the extended reach inspection apparatus further comprising a collar (204) attached to the shaft, the collar comprising a groove (206) for receiving and retaining the tether and allowing the shaft to rotate the probe.

18. The extended reach inspection apparatus of claim 14, further comprising a tether (107) coupled to the probe and to the scanner body, the tether retaining the probe with the scanner body in response to the probe being pulled from the scanner device.

19. The extended reach inspection apparatus of claim 14, further comprising:
   a camera (36) associated with the scanner device, wherein the camera is positioned with respect to an inspection probe (16) of the scanner device for positioning the inspection probe relative to a component (904) for inspection of the component; and
   a monitor (34) coupled to the camera for viewing an image of the component to be inspected and the robotic manipulator arm being movable to position the inspection probe relative to the component for inspection of the component.

20. The extended reach inspection apparatus of claim 1, further comprising:
   at least one intermediate arm segment between the proximal arm segment and the distal end arm segment; and
   a multi-axis movable joint that connects the at least one arm intermediate segment to each adjacent arm segment for articulating the arm segments relative to one another.

* * * * *